(12) United States Patent
Liao et al.

(10) Patent No.: US 8,712,184 B1
(45) Date of Patent: Apr. 29, 2014

(54) METHOD AND SYSTEM FOR FILTERING NOISES IN AN IMAGE SCANNED BY CHARGED PARTICLES

(75) Inventors: Chad Liao, Hsinchu (TW); Futang Peng, San Jose, CA (US); Chuan Li, San Jose, CA (US); Alina Wang, New Taipei (TW); Zhao-Li Zhang, San Jose, CA (US); Wei Fang, Milpitas, CA (US); Jack Jau, Los Altos Hills, CA (US)

(73) Assignee: Hermes Microvision, Inc., Hsinchu (TW)

( * ) Notice: Subject to any disclaimer, the term of this patent is extended or adjusted under 35 U.S.C. 154(b) by 102 days.

(21) Appl. No.: 13/311,043

(22) Filed: Dec. 5, 2011

(51) Int. Cl.
*G06K 9/40* (2006.01)
*G06K 9/00* (2006.01)
*G01N 23/00* (2006.01)

(52) U.S. Cl.
USPC .......................... 382/275; 382/149; 250/306

(58) Field of Classification Search
USPC ......... 382/149, 254, 260, 274–276, 305, 312; 704/233; 250/306, 310, 492.1; 702/39; 324/452; 356/237.2
See application file for complete search history.

(56) References Cited

U.S. PATENT DOCUMENTS

| | | | |
|---|---|---|---|
| 5,502,306 A * | 3/1996 | Meisburger et al. | 250/310 |
| 6,570,154 B1 * | 5/2003 | Masnaghetti et al. | 250/310 |
| 7,239,148 B2 * | 7/2007 | Suhara | 324/452 |
| 7,274,018 B2 * | 9/2007 | Adamec et al. | 250/310 |
| 7,633,061 B2 * | 12/2009 | Tanaka et al. | 250/306 |
| 7,783,433 B2 * | 8/2010 | Gordon et al. | 702/39 |
| 8,076,654 B2 * | 12/2011 | Hatakeyama et al. | 250/492.1 |
| 8,111,902 B2 * | 2/2012 | Hiroi et al. | 382/149 |
| 8,234,111 B2 * | 7/2012 | Lloyd et al. | 704/233 |
| 8,253,934 B2 * | 8/2012 | Yoshida et al. | 356/237.2 |
| 8,421,027 B2 * | 4/2013 | Barkshire et al. | 250/396 R |

* cited by examiner

*Primary Examiner* — Kanjibhai Patel
(74) *Attorney, Agent, or Firm* — Muncy, Geissler, Olds & Lowe, P.C.

(57) ABSTRACT

A method for filtering noises in an image scanned by charged particles includes steps of grouping pixels with similar types in the image into a plurality of pixel groups; and removing noises for each pixel group in the image according to a corresponding noise model to obtain the scanned image with better quality and/or contrast. A system for filtering noises in an image scanned by charged particles is also disclosed.

18 Claims, 5 Drawing Sheets

METHOD AND SYSTEM FOR FILTERING NOISES IN AN IMAGE SCANNED BY CHARGED PARTICLES

BACKGROUND OF THE INVENTION

1. Field of the Invention

The present invention relates to a method and a system for filtering noises, and more particularly to a method and a system for filtering noises in an image scanned by charged particles.

2. Description of the Prior Art

How to inspect defects on a semiconductor device is one of the major subjects in a semiconductor manufacturing process. A prior art method for inspecting defects includes capturing a scanned image of a semiconductor device, such as a scanning electron microscope (SEM) image, and then determining the presence of a defect of the semiconductor device in the scanned image. Therefore, it is very important to obtain an acceptable scanned image.

Referring to FIG. 1, a prior art method for scan imaging comprises scanning primary charged particles 101 across a surface of a sample, and detecting secondary charged particles 102 emitted from the surface of the sample being bombarded by the primary charged particles 101 to form a scanned image accordingly. However, backscattered charged particles 103 are also generated and detected, resulting in noises in scanning process. Traditionally, only one algorithm or noise model is applied to the scanned image to filter noise. However, for different materials on a semiconductor wafer, different noises are generated. Moreover, referring to FIG. 2, the probe spot 20 of the charged particles scans different patterns 22a and 22b along scanning paths 21a, 21b, and 21c or with different scanning directions, which results in different appearances of generated noises. Therefore, the prior art method using only one algorithm or noise model to filter noise cannot obtain a scanned image with better quality. Further, the traditional method for filtering noises is mostly for general electronic images, but is not applicable to an SEM image of wafer with specific characteristics.

Accordingly, it is highly desirable to filter different type noises to obtain a better quality image.

SUMMARY OF THE INVENTION

The present invention is directed to a method and a system for filtering noises in an image scanned by charged particles which filter noises for different type pixel groups in the image by a corresponding noise model so as to obtain a scanned image with better quality.

In a first embodiment, the proposed method for filtering noises in an image scanned by charged particles includes steps of grouping pixels with similar types in the image into a plurality of pixel groups; and removing noises for each pixel group in the image according to a corresponding noise model.

In a second embodiment, the proposed computer readable medium is encoded with a computer program implementing a method for filtering noises in an image scanned by charged particles, wherein the method includes steps of: grouping pixels with similar types in the image into a plurality of pixel groups; and removing noises for each pixel group in the image according to a corresponding noise model.

In a third embodiment, the proposed system for filtering noises in an image scanned by charged particles includes a charged particle beam probe generator, a charged particle beam deflection module, an image forming apparatus and a noise filtering module. The charged particle beam probe generator is configured for generating a charged particle beam probe. The charged particle beam deflection module is configured for scanning the charged particle beam probe across a surface of a sample. The image forming apparatus is configured for detecting secondary charged particles emitted from the surface of the sample being bombarded by the charged particle beam probe and forming at least one scanned raw image accordingly. The noise filtering module is encoded with a computer program implementing a method for filtering noises in an image scanned by charged particles, wherein the method comprises steps of: grouping pixels with similar types in the image into a plurality of pixel groups; and removing noises for each pixel group in the image according to a corresponding noise model.

In a fourth embodiment, the proposed system for filtering noises in an image scanned by charged particles includes means for grouping pixels with similar types in the image into a plurality of pixel groups; means for establishing different noise models corresponding to the plurality of pixel groups; and means for removing noises for each pixel group in the image according to the corresponding noise model.

The objective, technologies, features and advantages of the present invention will become apparent from the following description in conjunction with the accompanying drawings wherein certain embodiments of the present invention are set forth by way of illustration and example.

BRIEF DESCRIPTION OF THE DRAWINGS

The foregoing conceptions and their accompanying advantages of this invention will become more readily appreciated after being better understood by referring to the following detailed description, in conjunction with the accompanying drawings, wherein.

DESCRIPTION OF THE PREFERRED EMBODIMENT

The detailed explanation of the present invention is described as follows. The described preferred embodiments are presented for purposes of illustrations and description, and they are not intended to limit the scope of the present invention.

An image formed by detecting secondary charged particles emitted from a surface of a sample being bombarded by the primary charged particles includes true information and noises. For example, the charged particles may be electrons or protons. In one embodiment, the image may be obtained by using an E-beam inspection tool. The electron current of the E-beam inspection tool is very large compared to CD-SEM (critical dimension scanning electron microscope), such that a probe spot is large enough that inspection speed can be very fast, but the quality of the obtained image is worse. The present invention is proposed for filtering noises in an image scanned by charged particles to obtain a better quality image.

Figure 1:
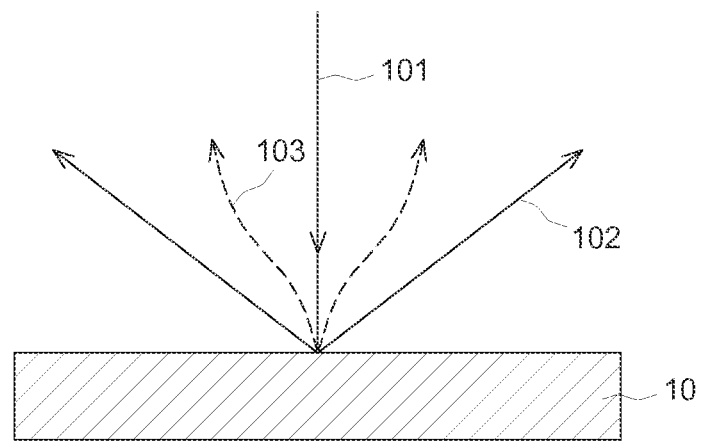
FIG. 1 is a diagram schematically illustrating a method for scan imaging by charged particles.
Figure 2:
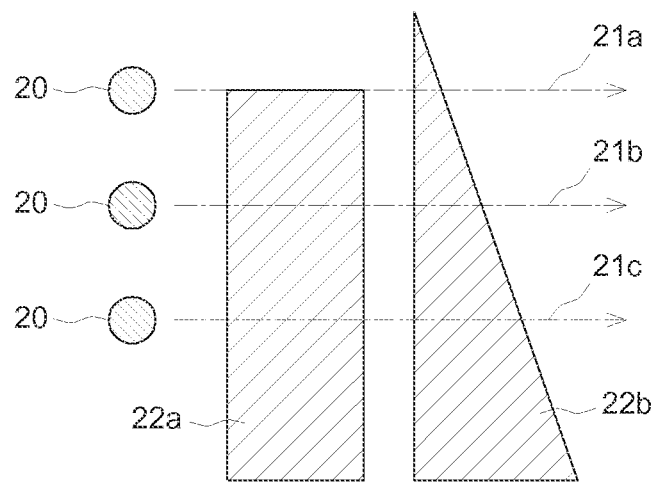
FIG. 2 is a diagram schematically illustrating influence of a scanning process on appearances of generated noises.
Figure 3:
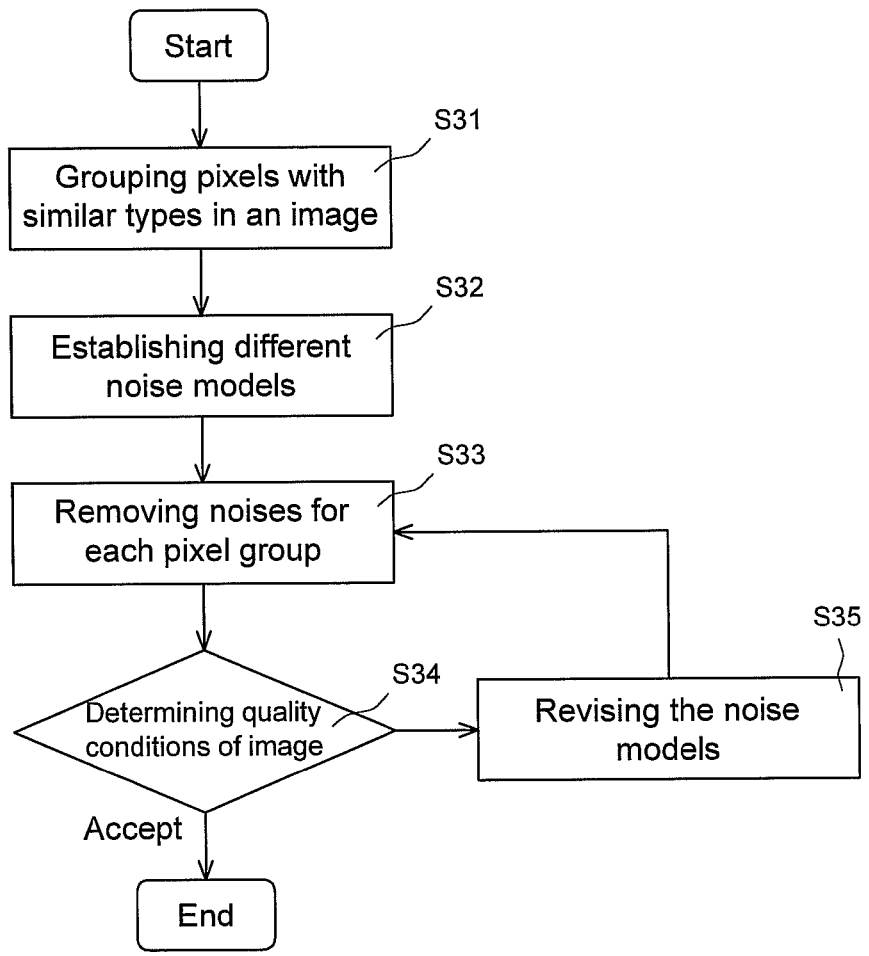
FIG. 3 is a flow chart schematically illustrating a method for filtering noises in an image scanned by charged particles according to an embodiment of the present invention.

A method for filtering noises in an image scanned by charged particles according to an embodiment of the present invention includes steps of grouping pixels with similar types in the image into a plurality of pixel groups; and removing noises for each pixel group in the image according to a corresponding noise model to obtain the image filtered noises. Referring to FIG. 3 for illustrated steps of a method for filtering noises without noise models according to an embodiment of the present invention. Firstly, pixels with similar types in an image scanned by charged particles are grouped into a plurality of pixel groups (S31). For example, referring to FIG. 2, the pixels obtained by scanning along the scanning path 21a are provided by similar features, i.e. they correspond to the upper edge of the pattern 22a. Therefore, the pixels corresponding to the upper edge of the pattern 22a can be grouped into the same pixel group. Similarly, the pixels obtained by scanning pattern 22a along the scanning path 21b and 21c can be grouped into the same pixel group based on the same width of the pattern 22a.

It should be noted that the noise appearances may be changed according to different widths of the pattern 22b; therefore the pixels obtained by scanning the pattern 22b along the scanning path 21b and 21c may be grouped into different pixel groups. In addition, the differences of material (such as silicon, silicon oxide, silicon nitride, polysilicon, silicide and metal etc.), pattern, edge between patterns, scanning environment and scanning direction may change the noise appearances, so the corresponding scanned pixels should be grouped into different pixel groups.

Figure 4:
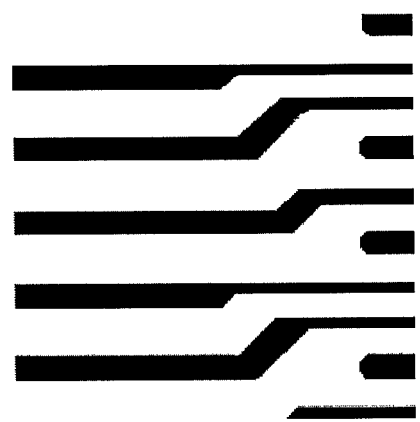
FIG. 4 is a diagram schematically illustrating a pattern in an image scanned by charged particles.

Next, different noise models corresponding to the plurality of pixel groups are established (S32). In one embodiment, the noise models may be filters, mapping data structures or a combination thereof. For example, the image shown in FIG. 4 can be represented by a mask and a Gaussian distribution. Therefore, the noise model can be a mathematical equation which is presented as $g_t(\mu_m, \sigma_m)$, wherein t represents the noise model revised t times by the loop shown in FIG. 3 and FIG. 5 (described below), $$\mu_m = \frac{\sum_{x_i \in X_m} x_i}{|X_m|}, \sigma_m = \sqrt{\frac{\sum_{x_i \in X_m} (x_i - \mu_m)^2}{|X_m|}}, m \in \{-1, +1\},$$

the category −1/+1 represents material type 1 or type 2, $x_i$ represents the image pixel, and $|X_m|$ represents the number of pixels of the category m in the image. It should be noted that the foregoing noise model is only for illustration purpose. It can be understood that a person skilled in the art can use other noise models to replace the foregoing noise model to achieve the same purpose.

Referring to FIG. 3 again, next, noises in each pixel group in the image are removed according to the corresponding noise model (S33). Because each noise model is established according to respective pixel groups, a better result of noise filtering can be achieved by using the noise model to remove noises for the corresponding pixel group in the image, which means an image with a better image quality can be obtained. In brief, noises in different pixel groups in the same image are filtered according to different noise models.

Finally, quality conditions of the filtered image are determined (S34). If the filtered image is still non-acceptable, then the flow goes to step S35 to revise the noise models. And then the flow goes back to step S33 to remove noises in the corresponding pixel groups according to the revised noise models, and goes to step S34 to determine the quality conditions of the filtered image. The steps S33 to S35 are iteratively performed until the filtered image is acceptable. For example, the filtered image is acceptable when the quality conditions of the image are not varying with an iteration of the step S33. Alternatively, the filtered image is also acceptable when the quality conditions of the image are accepted or within a threshold value after iteratively performing the step S33. For example, if a grey level slope of pixels from light to dark or form dark to light is within the determined threshold value, the filtered image is acceptable. According to the foregoing steps, not only the image with better quality can be obtained but also the corresponding noise models can be revised gradually and stored in a database for the next operation of filtering noises.

Figure 5:
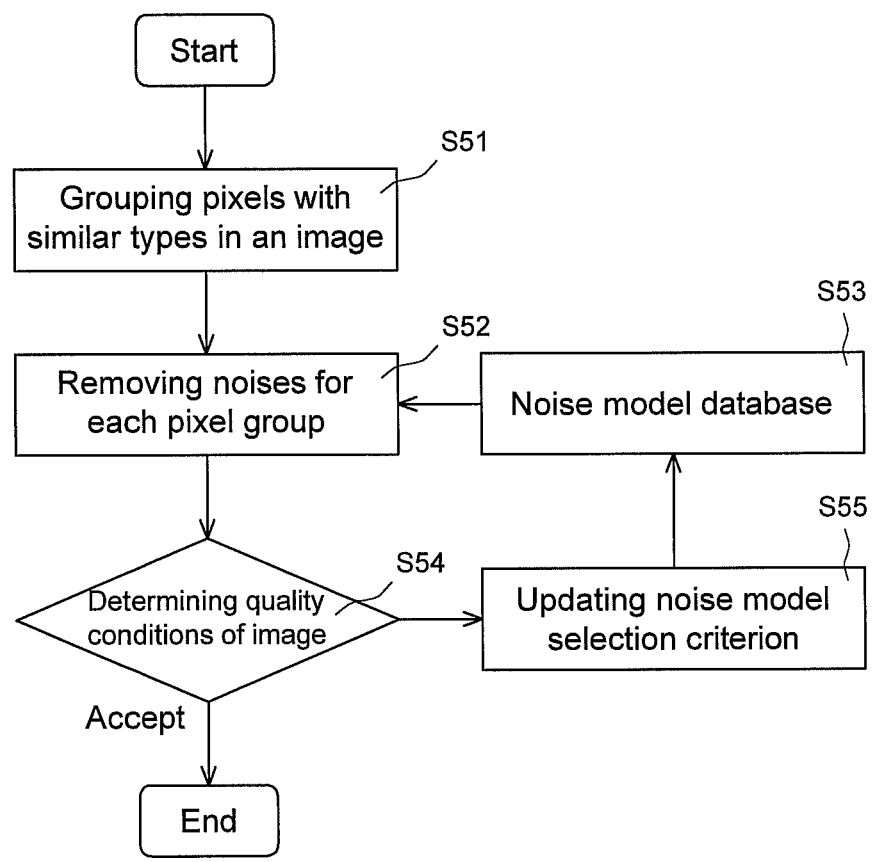
FIG. 5 is a flow chart schematically illustrating a method for filtering noises in an image scanned by charged particles according to another embodiment of the present invention.

Referring to FIG. 5 for illustrated steps of a method for filtering noises with noise models according to an embodiment of the present invention. Firstly, pixels with similar types in an image scanned by charged particles are grouped into a plurality of pixel groups (S51), and noises in each pixel group are removed (S52) by the corresponding noise models in a database (S53). Next, quality conditions of the filtered image are determined (S54). If the filtered image is acceptable, then the method according to the embodiment of the present invention is stopped. If the filtered image is not acceptable, then the other noise models computed and stored in advance can be selected to remove noises, i.e. noise model selection criterion can be updated (S55), and stored in the noise model database (S53). It should be noted that, in another embodiment, the noise models can be revised and stored in the noise model database (S53). And then, the flow goes back to step S52 to remove noises in the corresponding pixel groups according to the revised noise models, and goes to step S54 to determine the quality conditions of the filtered image. The steps S52 to S55 are iteratively performed until the filtered image is acceptable. The detail description of the steps has been provided above and would be skipped here.

In one embodiment, a computer readable medium of the present invention is encoded with a computer program. The computer program implements a method for filtering noises in an image scanned by charged particles. Detail implementing steps of the method of the present invention has been described previously and will not be repeated here.

Figure 6:
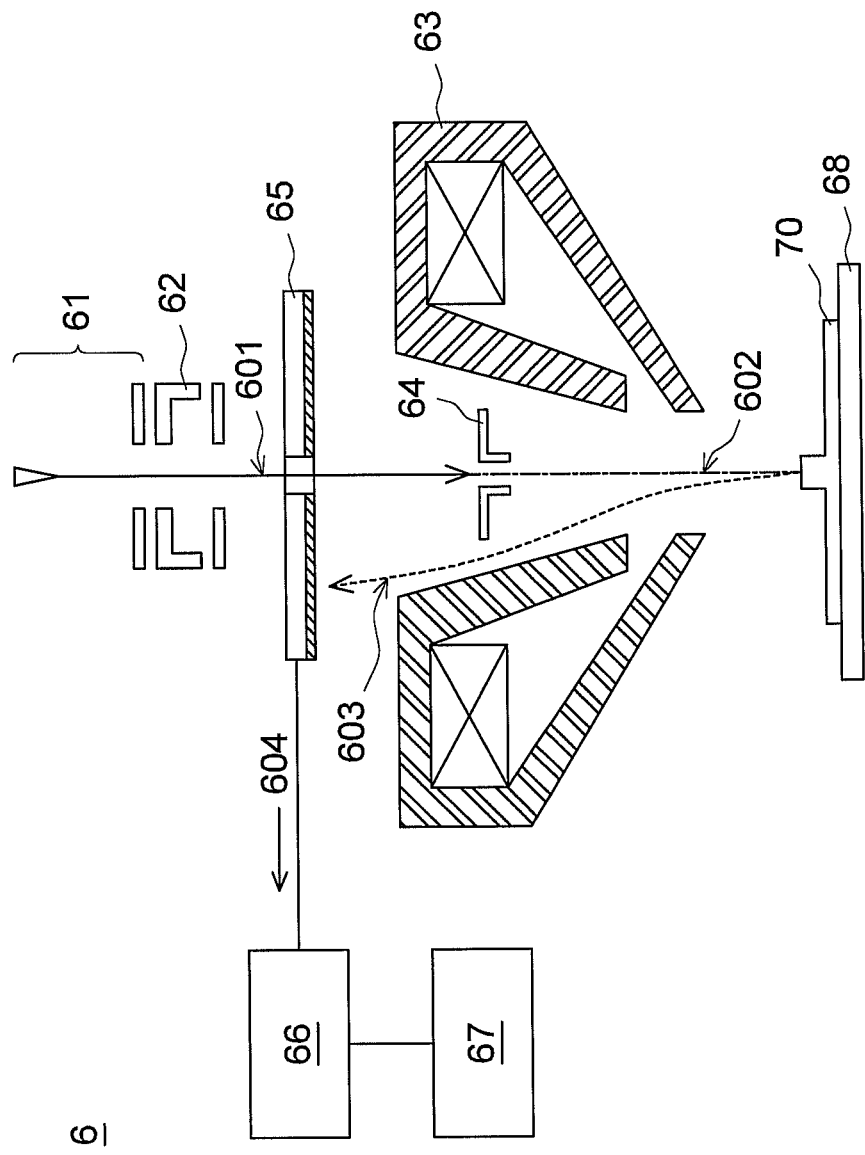
FIG. 6 is a diagram schematically illustrating a system for filtering noises in an image scanned by charged particles according to an embodiment of the present invention.

Please refer to FIG. 6 which illustrates a system 6 for filtering noises in an image scanned by charged particles according to an embodiment of the present invention. The system 6 is used for inspecting a sample 70 (such as a wafer) on a sample stage 68 and comprises a charged particle beam generator 61, a condenser lens module 62, a probe forming objective lens module 63, a charged particle beam deflection module 64, a secondary charged particle detector module 65, an image forming module 66 and a noise filtering module 67.

The charged particle beam generator 61 is used for generating a primary charged particle beam 601. The condenser lens module 62 is used for condensing the generated primary charged particle beam 601. The probe forming objective lens module 63 is used for focusing the condensed primary charged particle beam into a charged particle beam probe 602. The charged particle beam deflection module 64 is used for scanning the formed charged particle beam probe 602 across surfaces of the sample 70 secured on the sample stage 68. In one embodiment, the charged particle beam generator 61, the condenser lens module 62 and the probe forming objective lens module 63, or their equivalent designs, alternatives or any combination thereof, together form a charged particle beam probe generator which generates the scanning charged particle beam probe 602.

The secondary charged particle detector module 65 is used for detecting secondary charged particles 603 emitted from the sample surface (may also be along with other reflected or scattered charged particles from the sample surface) upon being bombarded by the charged particle beam probe 602 and generating a secondary charged particle detection signal 604. The image forming module 66 is coupled with the secondary charged particle detector module 65 for receiving the secondary charged particle detection signal 604 from the secondary charged particle detector module 65 and forming at least one scanned raw image accordingly.

The image forming module 66 may be a mainframe host, terminals, personal computers, any kind of mobile computing devices or combination thereof. In addition, the image forming module 66 may connect with the secondary charged particle detector module 65 through a medium selected from the following: cable wire, optical fiber cable, portable storage media, IR, Bluetooth, intranet, internet, wireless network, wireless radio, and any combination thereof. In one embodiment, the secondary charged particle detector module 65 and image forming module 66, or their equivalent designs, alternatives or any combination thereof, together form an image forming apparatus which forms a scanned raw image from detected secondary charged particles emitted from sample 70 being bombarded by the charged particle beam probe 602.

The above components of the system are well known to those skilled in the art and are not presented here to limit the scope of the present invention. Alternatives, and insubstantial modifications of these components should be construed equivalent to the disclosure of the present invention.

The noise filtering module 67 is coupled to the image forming module 66 of the image forming apparatus to filter noises in the scanned raw image received from the image forming module 66. In one embodiment, the noise filtering module 67 connects to and accesses the image forming apparatus through a medium selected from the following: cable wire, optical fiber cable, portable storage media, IR, manual input of humans, Bluetooth, intranet, internet, wireless network, wireless radio, and any combination thereof. Further, the noise filtering module 67 may be implemented as one selected from the following: a mainframe host, a terminal computer, a personal computer, any kind of mobile computing devices, and any combination thereof. In one embodiment, a computer program for filtering noises in an image scanned by charged particles is encoded on a computer readable medium disposed within the noise filtering module 67 so that the noise filtering module 67 is able to perform the steps of filtering noises in the image illustrated in conjunction with FIG. 3 or FIG. 5, wherein the details of the steps of filtering noises in the image scanned by charged particles are described earlier.

To summarize the foregoing descriptions, the method and system for filtering noises in an image scanned by charged particles filter noises in different type pixel groups according to corresponding noise models, so that the scanned image with better quality and/or contrast is obtained. In addition, the following advantages can be achieved:

1) Knowledge such as noise model and quality conditions etc. can be stored, updated and reused.

2) Higher detection rate and lower false alarm of the subsequent inspection can be achieved based on better image quality.

3) The scanned image with better quality can be obtained by using E-beam inspection tool with lower resolution such that the demand of hardware for image acquisition and defect inspection is lower.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the spirit and scope of the appended claims.

What is claimed is:

1. A method for filtering noises in an image generated by a scanning device using charged particles to scan, comprising steps of:
   grouping pixels with similar types in the image into a plurality of pixel groups; and
   removing noises for each pixel group in the image according to a corresponding noise model;
   establishing different noise models corresponding to the plurality of pixel groups after the grouping step;
   determining quality conditions of the image;
   wherein the filtered image is acceptable when the quality conditions are accepted or within a threshold value after performing the removing step.

2. The method according to claim 1, wherein the noise models comprise filters, mapping data structures or a combination thereof.

3. The method according to claim 1, wherein the filtered image is acceptable when the quality conditions are not varying with an iteration of the removing step.

4. The method according to claim 1, wherein the quality conditions are used for revising the noise models.

5. The method according to claim 1, wherein the charged particles are electrons or protons.

6. The method according to claim 1, wherein the image is obtained by using an E-beam inspection tool.

7. A non-transitory computer readable storage medium, encoded with a computer program implementing a method for filtering noises in an image scanned generated by a scanning device using charged particles to scan, wherein the method comprises steps of:
   grouping pixels with similar types in the image into a plurality of pixel groups; and
   removing noises for each pixel group in the image according to a corresponding noise model;
   establishing different noise models corresponding to the plurality of pixel groups after the grouping step;
   determining quality conditions of the image;
   wherein the filtered image is acceptable when the quality conditions are accepted or within a threshold value after performing the removing step.

8. The non-transitory computer readable storage medium according to claim 7, wherein the noise models comprise filters, mapping data structures or a combination thereof.

9. The non-transitory computer readable storage medium according to claim 7, wherein the filtered image is acceptable when the quality conditions are not varying with an iteration of the removing step.

10. The non-transitory computer readable storage medium according to claim 7, wherein the quality conditions are used for revising the noise models.

11. The non-transitory computer readable storage medium according to claim 7, wherein the charged particles are electrons or protons.

12. The non-transitory computer readable storage medium according to claim 7, wherein the image is obtained by using an E-beam inspection tool.

13. A system for filtering noises in an image generated by a scanning device using charged particles to scan, comprising:
- a charged particle beam probe generator for generating a charged particle beam probe;
- a charged particle beam deflection module for scanning the charged particle beam probe across a surface of a sample;
- an image forming apparatus for detecting secondary charged particles emitted from the surface of the sample being bombarded by the charged particle beam probe and forming at least one scanned raw image accordingly; and
- a noise filtering module encoded with a computer program implementing a method for filtering noises in an image generated by a scanning device using charged particles to scan, wherein the method comprises steps of:
- grouping pixels with similar types in the image into a plurality of pixel groups; and
- removing noises for each pixel group in the image according to a corresponding noise model;
- establishing different noise models corresponding to the plurality of pixel groups after the grouping step;
- determining quality conditions of the image;
- wherein the filtered image is acceptable when the quality conditions are accepted or within a threshold value after performing the removing step.

14. The system according to claim 13, wherein the noise models comprise filters, mapping data structures or a combination thereof.

15. The system according to claim 13, wherein the filtered image is acceptable when the quality conditions are not varying with an iteration of the removing step.

16. The system according to claim 13, wherein the quality conditions are used for revising the noise models.

17. The system according to claim 13, wherein the charged particles are electrons or protons.

18. A system for filtering noises in an image generated by a scanning device using charged particles to scan, comprising:
- means for grouping pixels with similar types in the image into a plurality of pixel groups;
- means for establishing different noise models corresponding to the plurality of pixel groups;
- means for removing noises for each pixel group in the image according to the corresponding noise model; and
- means for determining quality conditions of the image;
- wherein the filtered image is acceptable when the quality conditions are accepted or within a threshold value after performing the removing step.

* * * * *